United States Patent
Dorn (10) Patent No.: US 10,423,655 B2
(45) Date of Patent: Sep. 24, 2019

(54) METHOD FOR PROCESSING DOSE INFORMATION IMAGES

(71) Applicant: Karlheinz Dorn, Kalchreuth (DE)

(72) Inventor: Karlheinz Dorn, Kalchreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 286 days.

(21) Appl. No.: 15/375,371

(22) Filed: Dec. 12, 2016

(65) Prior Publication Data

US 2017/0177570 A1 Jun. 22, 2017

(30) Foreign Application Priority Data

Dec. 17, 2015 (DE) .................. 10 2015 225 735

(51) Int. Cl.
| | | |
|---|---|---|
| G06F 17/30 | (2006.01) | |
| G06F 16/51 | (2019.01) | |
| G16H 10/60 | (2018.01) | |
| G06F 16/58 | (2019.01) | |
| G06F 16/28 | (2019.01) | |
| G06F 19/00 | (2018.01) | |
| G06T 7/00 | (2017.01) | |
| G06F 16/583 | (2019.01) | |

(52) U.S. Cl.
CPC .......... G06F 16/51 (2019.01); G06F 16/285 (2019.01); G06F 16/5866 (2019.01); G06F 19/321 (2013.01); G16H 10/60 (2018.01); G06F 16/5838 (2019.01); G06T 7/0012 (2013.01)

(58) Field of Classification Search
CPC .. G06F 19/321; G06F 19/00; G06F 17/30598; G06F 19/3418; G06F 19/3481; G06F 17/30256; G06F 19/325; G06F 3/04842; G06F 3/04845; G06T 7/0012; G06T 11/005; G06T 2207/10081; G06T 2207/10101; G06T 7/00; G16H 40/63; G16H 30/20
USPC ................ 707/772, 736, 740, 758, 770, 777
See application file for complete search history.

(56) References Cited

U.S. PATENT DOCUMENTS 8,412,544 B2 * 4/2013 Reiner .................. G06F 19/321
 705/3
9,177,102 B2 * 11/2015 Bower .................. G06F 19/321
(Continued)

OTHER PUBLICATIONS

German office Action for related German Application No. 10 2015 225 735.5 dated Nov. 18, 2016, with English Translation.

*Primary Examiner* — Dangelino N Gortayo
(74) *Attorney, Agent, or Firm* — Lempia Summerfield Katz LLC (57) ABSTRACT

The present disclosure relates to methods for automatically controlling loading processes of dose information images. In one example, the method includes receiving a data record at a local data repository, wherein the data record contains a dose information image and a scanner index. The method further includes: comparing the scanner index against a whitelist from the central data repository; transmitting the data record from the local data repository to a checking directory of the central data repository when the scanner index is not contained in the whitelist; validating the dose information image from the checking directory by character recognition; and entering the scanner index in the whitelist in the event of successful validation of the dose information image.

15 Claims, 4 Drawing Sheets

(56) References Cited

U.S. PATENT DOCUMENTS

| | | | |
|---|---|---|---|
| 9,235,889 B1* | 1/2016 | Frenkel | G06F 19/321 |
| 2005/0117527 A1* | 6/2005 | Williams | G06Q 10/10 |
| | | | 370/260 |
| 2010/0021027 A1 | 1/2010 | Hartkens et al. | |
| 2013/0102853 A1* | 4/2013 | Halvorson | G06F 19/00 |
| | | | 600/300 |
| 2013/0208966 A1 | 8/2013 | Zhao et al. | |
| 2013/0243300 A1* | 9/2013 | Oda | G06T 7/0012 |
| | | | 382/132 |
| 2014/0075520 A1 | 3/2014 | Subramanian et al. | |
| 2014/0270053 A1* | 9/2014 | Larson | A61B 6/032 |
| | | | 378/4 |
| 2015/0100572 A1 | 4/2015 | Kalafut et al. | |
| 2015/0227591 A1* | 8/2015 | Jose | G06F 16/285 |
| | | | 707/777 |
| 2015/0356258 A1* | 12/2015 | Moore | G06F 19/3481 |
| | | | 705/2 |
| 2016/0004818 A1* | 1/2016 | Seifert | G06F 19/321 |
| | | | 705/3 |

* cited by examiner

```
Exam Information
Study ID:                64060
Time:                    Jul 22, 2015, 08:42
Total DLP:               492.6 mGy*cm Dose

Description        Scan        mAs  kV   CTDIvol    DLP     Phantom
                       Mode                  [mGy]      [mGy*cm] Type [cm]
  2                    Surview       1  120     0.09      4.3    32 CM
  3 LOCATOR            Stationary  N/A  120     2.41      2.4    32 CM
  4 tracker            Stationary  N/A  120     7.24      7.2    32 CM
  5                    Helical     200  120    13.08    478.7    32 CM
```

METHOD FOR PROCESSING DOSE INFORMATION IMAGES

This application claims the benefit of DE 10 2015 225 735.5, filed Dec. 17, 2015, which is hereby incorporated by reference in its entirety.

TECHNICAL FIELD

The present disclosure relates to a method and a system for processing dose information images.

BACKGROUND

In present systems, a user detects an error in a generating system that is caused by particular manufacturer-specific dose information images. Several manual checks outside the production system are required until remedial action shows correct support of a dose information image type. No controlled or automated assistance exists for detecting problems with dose information image types of different manufacturers' CT equipment in a production system. In addition, there exists no controlled or automated facility for re-using dose information images of CT scanners once the support is confirmed.

There is no information for operators of supported and unsupported dose information images of CT scanners. This makes it more difficult to automatically detect unsupported CT scanners and prevents uploading of dose information images to the cloud. No operator information about supported or unsupported dose information images for specific scanner types is provided.

SUMMARY AND DESCRIPTION

The scope of the present disclosure is defined solely by the appended claims and is not affected to any degree by the statements within this summary. The present embodiments may obviate one or more of the drawbacks or limitations in the related art.

The object of the present disclosure is to provide a uniform mechanism enabling new CT scanners of different manufacturers to be reliably connected to a central dose management system in respect of dose information image support.

According to a first aspect, this object is achieved by a method for automatically controlling dose information image loading processes. The method includes: receiving a data record at a local data repository, the data record containing a dose information image and a scanner index; comparing the scanner index against a whitelist from the central data repository; transmitting the data record from the local data repository to a checking directory of the central data repository if the scanner index is not contained in the whitelist; validating the dose information image from the checking directory using character recognition; and entering the scanner index in the whitelist if the dose information image is successfully validated. The checking directory may be constituted by a container.

In an advantageous embodiment of the method, the data record is transmitted from the local data repository to a non-checking directory of the central data repository if the scanner index is contained in the whitelist. The non-checking directory may be constituted by a container.

In another advantageous embodiment of the method, the whitelist is stored in the central data repository.

In another advantageous embodiment of the method, the whitelist is transmitted to the local data repository.

In another advantageous embodiment of the method, the checking directory is cyclically scanned for new data records.

In another advantageous embodiment of the method, uploading of data records to a non-checking directory is suspended if the scanner index is not contained in the whitelist.

In another advantageous embodiment of the method, the data record is assigned a validation status.

According to a second aspect, the object is achieved by a system for automatically controlling dose information image loading operations. The system includes an uploader for receiving a data record at a local data repository, wherein the data record contains a dose information image and a scanner index, comparing the scanner index against a whitelist from the central data repository, and transmitting the data record from the local data repository to a checking directory of the central data repository if the scanner index is not contained in the whitelist. The system also includes a validator for validating the dose information image by character recognition and for entering the scanner index in the whitelist in the event of successful validation of the dose information image.

In another embodiment of the system, the system is capable of entering the scanner index in the whitelist if the dose information image was successfully validated.

According to a third aspect, the object is achieved by a computer program product that may be loaded into the memory of a computer and include code sections for carrying out the method according to the first aspect when the computer program product is executed by the computer.

BRIEF DESCRIPTION OF THE DRAWINGS

Exemplary embodiments, which will now be explained in greater detail, are illustrated in the accompanying drawings in which.

DETAILED DESCRIPTION

Figure 1:
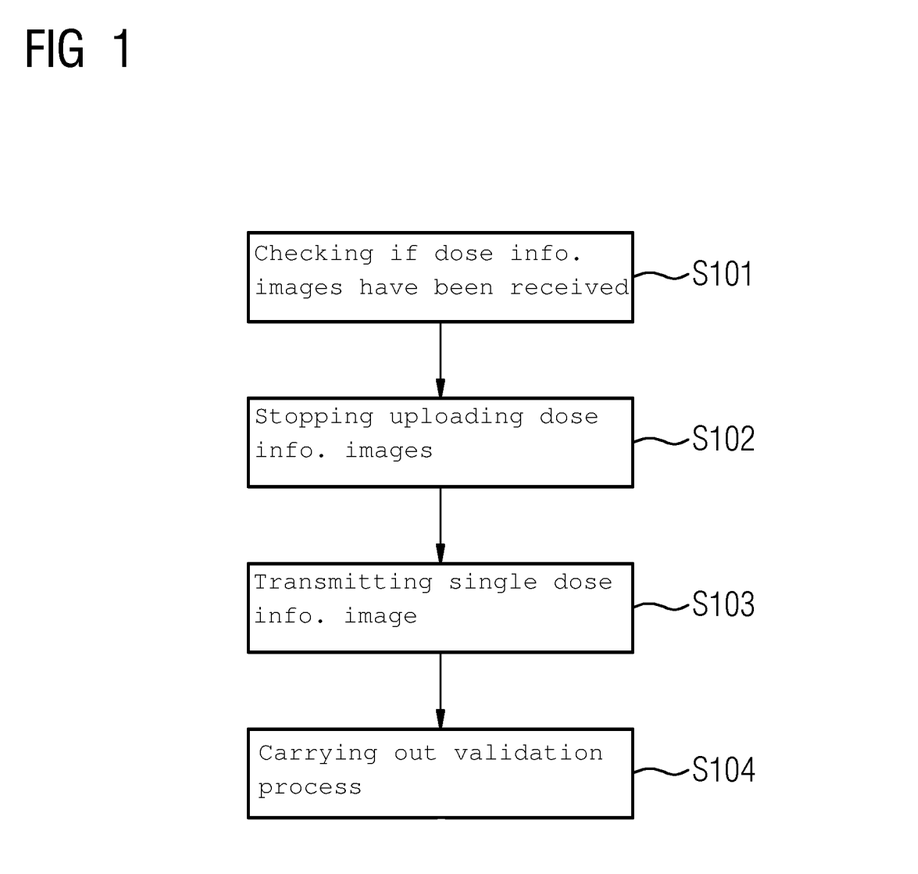
FIG. 1 depicts a block diagram of a method according to an example.

FIG. 1 depicts a block diagram of a method for automatically controlling loading processes of dose information images ("black images"). The dose information images are digital image files containing information concerning a radiation dose, a date, a time of day, and/or a study ID.

In act S101, an uploader checks in a local data repository whether dose information images have been received from a known CT scanner that is part of an entry in a whitelist of CT scanners. The CT scanner is identifiable, for example, by a scanner index containing information concerning an operator, a manufacturer, a manufacturer model, a secondary capture type, a software version, or an equipment serial number.

In act S102, the uploader stops uploading dose information images to the central data repository (e.g., "cloud") if they have not been received from a known CT scanner. Whether the CT scanner is known may be ascertained based on a comparison between the whitelist and the scanner index.

In act S103, the uploader transmits a single dose information image together with the associated scanner index to the central data repository and stores it in a greylist container for unknown CT scanners. The greylist container may be set up for each CT scanner operator or may be a global greylist container in the central data repository that stores a single original Digital Imaging and Communications in Medicine (DICOM) file for each scanner version.

In act S104, an automatic validation process for the dose information images in the greylist container is carried out. For this purpose, the greylist container is scanned using additional tools. For this validation, the dose information image is scanned using automatic character recognition ("OCR").

Each CT scan is based on two fundamental dose calculation equations.

$$\text{Single dose} = \text{average dose} * \text{scan length} \quad (1)$$

$$\text{Total dose} = \text{sum of the single doses} \quad (2)$$

The dose information images include all the elements of these equations as well as the total dose in pictorial form. The mechanism therefore uses the following preconditions to check the plausibility and correctness of a dose information image in respect of the dose information.

The preconditions are: (1) All the individual elements for the two equations are present in the dose information image; (2) The total dose is part of the dose information image; (3) The number of individual doses is part of the dose information image.

Consequently, there are two possibilities for mathematically checking the result of previously performed text recognition in respect of plausibility.

In one possibility, the sum of all the single doses yields the total dose.

In a second possibility, the product of single dose and scan length of each single dose summed over all the single doses likewise yields the total dose.

These two checking options allow sufficient plausibility checking that the character recognition mechanism has provided correct results for the dose information image.

Accordingly, if the above-mentioned conditions are checked and approximately the same value is obtained mathematically for the total dose, the value having been obtained on the basis of automatic character recognition, accurate character recognition may be assumed. However, in the event of deviations exceeding a predefined value, it is assumed that automatic character recognition has produced incorrect results and the dose values cannot be reliably used.

A positively validated CT scanner is entered in the whitelist and is viewable in a whitelist/blacklist tool. Only positively validated CT scanners are permitted to upload dose information images to the central data repository.

Figure 2:
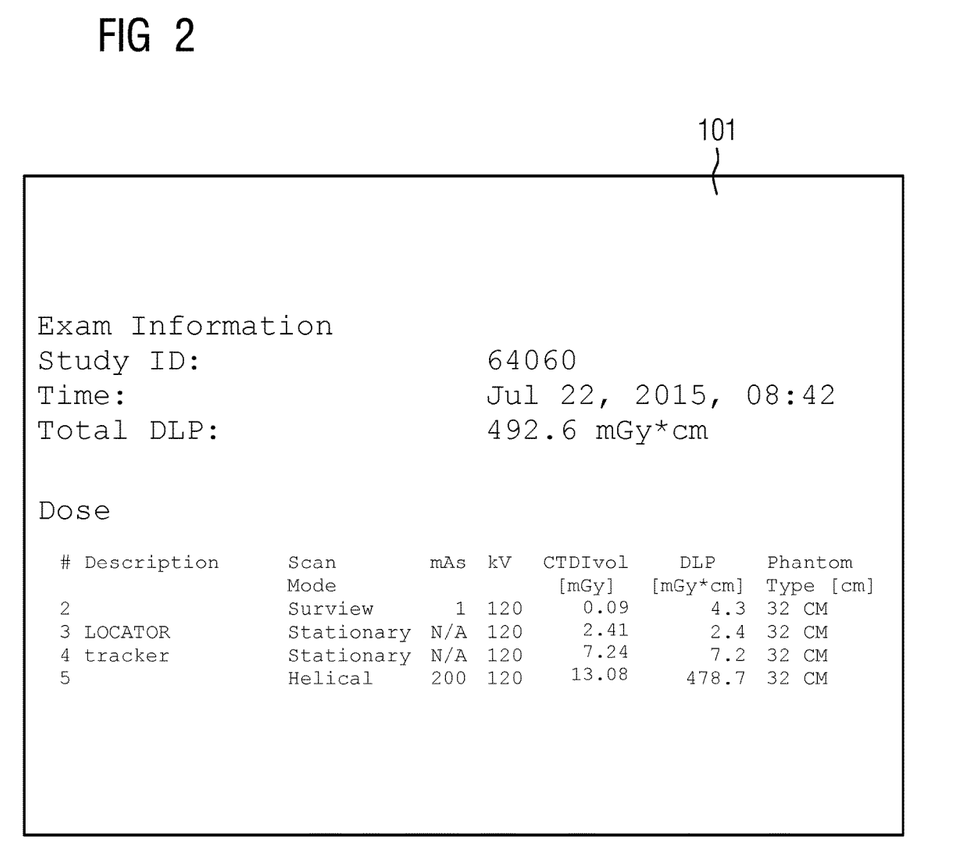
FIG. 2 depicts an example of a dose information image.

FIG. 2 depicts a dose information image 101 of a CT scanner. The dose information images 101 are generated by computed tomography devices (e.g., CT scanners). Depending on the scanner manufacturer, these may contain different information in different layouts and using different fonts. The dose information image 101 is a secondary image format and is stored in a DICOM file with associated media type. The dose information image 101 is designed to be human readable to ascertain the dose information.

Figure 3:
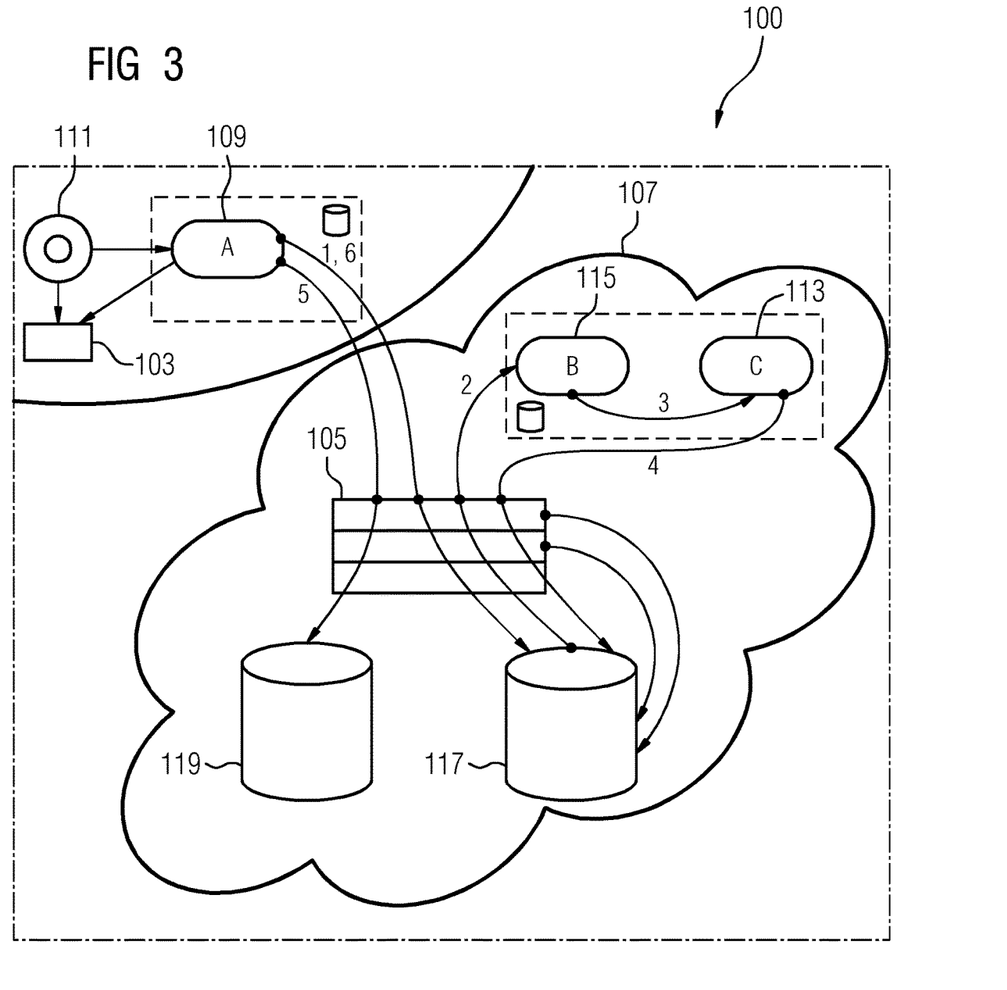
FIG. 3 schematically illustrates an example of a system.

FIG. 3 depicts a system 100 for automatically controlling loading processes of dose information images 101. The system includes a CT scanner 111 for a medical X-ray examination. The dose information image 101 with the above-mentioned information is transmitted from the CT scanner 111 to a local data repository 103 such as hospital's picture archiving and communication system (PACS) in a data record together with the scanner index for identifying the CT scanner 111.

In the local data repository 103, the uploader 109 is implemented by a computer program capable of transmitting the data records of the CT scanners 111 to a central data repository 107 (e.g., "cloud"). The local data repository 103, such as a hard disk, for example, may be part of a computer system including a processor and random access memory. However, this only occurs if comparison of the scanner index against a whitelist 109 shows that the CT scanner is known.

If it is not known, e.g., the scanner index is not in the whitelist, only a single data record containing a dose information image and a scanner index is transmitted to a checking directory of the central data repository 107. The dose information image 101 is validated automatically in the central data repository 107. If validation by the validator 113 is successful, the scanner index is entered in the whitelist. The central data repository 107, (e.g., a hard disk system), may be part of a computer system including processors and random access memory. The central data repository includes a checking directory 117 and a non-checking directory 119.

A) Greylist Uploader in the Application (Receiver)

a) Generating of a scanner index for the CT scanner of an operator ("tenant") from a particular scanner manufacturer.

b) Checking (reading) of the scanner index (if present) for CT scanner x of manufacturer y and executable for an operator of the CT device having a particular software version against a whitelist/blacklist of stored scanner indices that may assume different statuses, e.g., "unknown", "in work", "bad" (not supported), "ok" (fully supported).

c) Setting the scanner index status to "unknown" if the scanner index is not present in the whitelist in the central repository and simultaneously one-off uploading of a dose information image 101 to the checking directory in the central data repository 107.

d) Suspending the uploading of dose information images 101 that come directly from CT scanners or from the operator's PACS system to the regular non-checking directory in the central data repository 107 as long as the scanner index does not have "ok" status.

e) This check is repeated each time a new dose information image 101 arrives, so that a change to "ok" status is noticed immediately, causing saving of the dose information image 101 in the regular non-checking directory ("study container") to be (re-)commenced. The greylist uploader of the application has no effect on this, but registers changes directly and then immediately switches over the processing of the dose information image 101 for the corresponding scanner index.

B) Greylist Downloader as a Central Service or in a Separate Computer a) Cyclical checking of the whitelist to ascertain whether the scanner index is present in the "unknown" status.

b) If so, the scanner index is read and its status is set to "in work", and the data associated with the scanner index is loaded by a reference in the scanner index from the central data repository 107 to a memory that may be accessed by a subsequent validation process.

C) Validation of the Dose Information Image 101 a) Accesses the dose information image 101 that has been loaded from the checking directory and performs automatic dose checking.

b) The dose checker reads the data of the dose information image 101 and uses OCR to generate the dose data contained therein.

c) Using horizontal and vertical checksum calculation, plausibility checks are carried out on the dose data so that their correctness may be verified.

d) As the result of this checking, the status of the scanner index is set to either "ok" or "bad" in the central data repository 107.

e) In addition, the results of the checking are restored as a text file in the checking directory of the central data repository 107 under the entry referenced by the scanner index so that they may be reproduced at any time from the other end.

The individual actions are performed by the independent software components as described below.

In act 0, the application/receiver receives a dose information image 101 directly from CT scanner 111 or actively requests them from the operator's PACS system, and creates therefrom the scanner index from the DICOM data of the dose information image 101 that provides the CT scanner 111 of the scanner manufacturer with a serial number and a software version, because it is currently in operation with this unambiguously specified operator and dose information images 101 are regularly received from this operator either directly or indirectly via PACS, e.g., 50 per day.

In act 1, the application/receiver checks by a central whitelist/blacklist whether the scanner index resulting from the dose information image 101 currently being processed has "ok" status, or is present at all. If it is not present, the scanner index is re-entered under "unknown" status. The dose information image is stored in the central data repository 107 and a reference thereto is likewise stored in the scanner index in the central index store.

In addition, the storing of dose information images 101 of this CT scanner 111 and operator is suspended until further notice, namely until such time as, for each new arrival of a dose information image 101 of this CT scanner, there is the status "ok" when checking in the central index store. From this time onwards, all the dose information images 101 of this CT scanner 111 of this operator are then loaded again to the non-checking directory (e.g., "study container") of the central data repository 107 because it may now be assumed that the dose information images 101 contain correctly determined dose values.

In act 2, independently of the processing on the application/receiver on the operator's premises, there is a downloader 115 that permanently checks the central index store to ascertain whether it contains scanner index entries having "unknown" status that are waiting to be checked by a central service. If such entries are found, the associated data of the dose information image 101 of the checking directory 117 in the central data repository 107 may be accessed by the reference stored in the scanner index entry and this may—if necessary—be copied to an environment that may be accessed by the validation act for checking the dose. This may be either in the central data repository 107 or in another computer or virtual machine.

In act 3, dose checking of a dose information image 101 is then carried out by a validation program. This check is fully automated. The validator ascertains whether the dose check on this dose information image was "ok" or "bad".

In act 4, the result of this automatic check is entered in the central index by the validation mechanism under the scanner index entry. It additionally stores the data generated during the dose check in the checking directory 117 (known by reference in the scanner index) of the central data repository 107.

In act 5, the next time a dose information image 101 of this CT scanner 101 is received, the application/receiver on the operator's premises detects that, in a routine check of the scanner index, the status thereof has changed. If the status has changed to "ok", the uploader of the operator's application/receiver will change its procedure such that, from now on, dose information images 101 for this CT scanner 111 are sent to the regular non-checking directory 119 of the central data repository 107 and are released for further processing and evaluation of the dose information.

In act 6, if the CT scanner 111 is subsequently provided with a new software version at the operator's premises, the scanner index changes automatically, as the software version of the CT scanner is an integral part of the scanner index.

This automatically means that the described method begins again at the first act. This is helpful because changing the software version of the CT scanner 101 may also change the font associated with the dose information image, or dose information images 101 may be changed from monochrome to color. As a result, it would no longer be provided that the dose check carried out remains valid. The automatic method described may therefore continue to operate correctly even in the event of changed environmental conditions in that a new dose check via the checking directory 117 temporarily stops regular processing via the non-checking directory (e.g., until the further dose check is successful).

Figure 4:
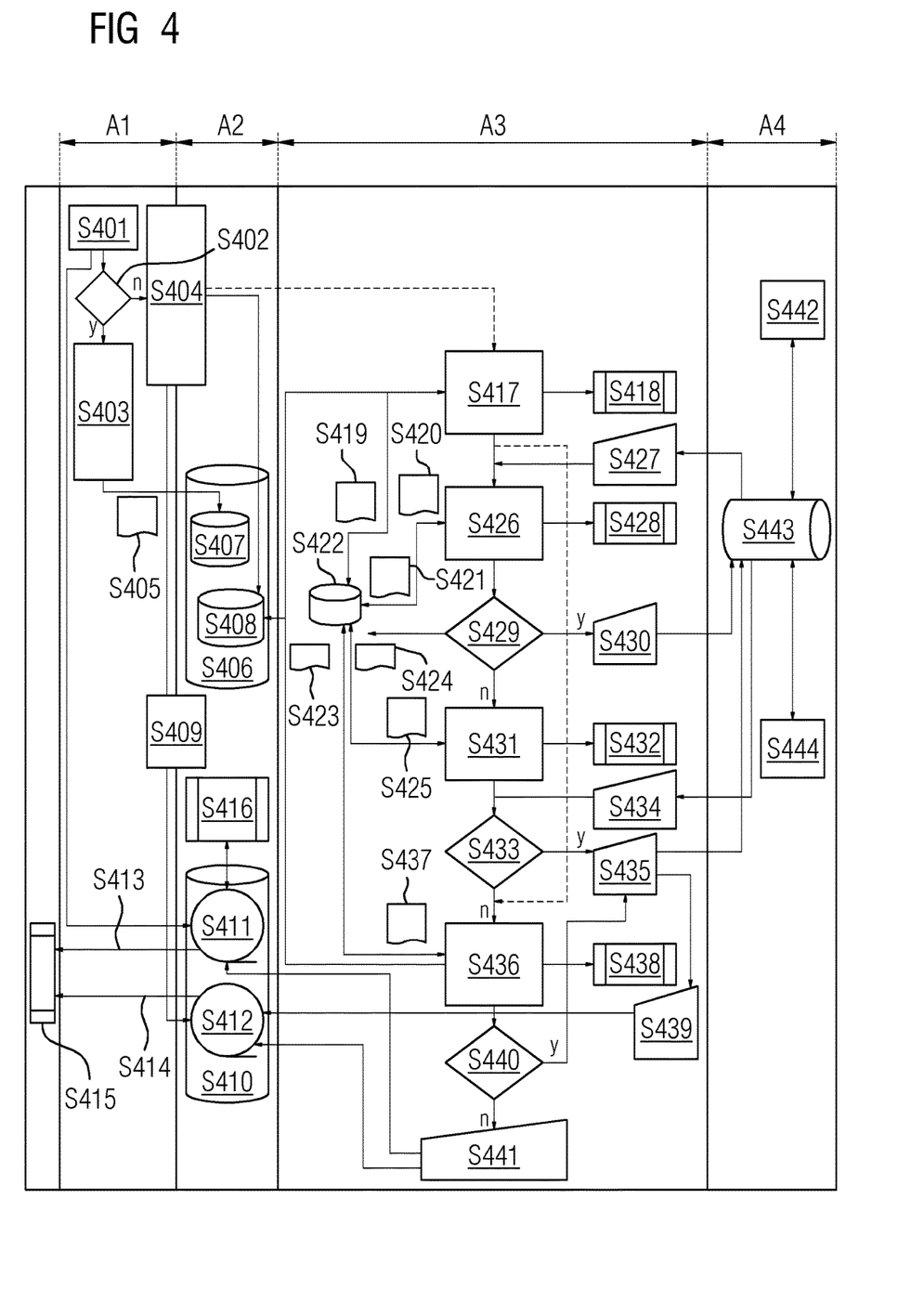
FIG. 4 depicts a flow chart according to an example.

FIG. 4 depicts a flow chart. In act S401, the scanner index is searched for. In act S402, it is checked whether the scanner index is in the whitelist. If the scanner index is in the whitelist, in act S403, normal uploading of protected healthcare information (PHI) dose information images of this scanner index to the central data repository is continued. If the scanner index is in the whitelist, in act S404, uploading of dose information images for this scanner index is stopped and the dose information image from the study is loaded into the greylist container as an original.

S405 denotes a PHI dose information image. S406 denotes a central data repository having a data memory S407 and a greylist container S408. In act S409, the scanner index is blacklisted.

S410 denotes a database having a whitelist S411 containing scanner indices and a blacklist S412 containing scanner indices. In act S413, customer information (e.g., app+email) is generated. In act S414, customer information is likewise generated. S415 denotes an HTML application for the whitelist. In act S416, a platform website is generated.

Act S417 is started on request. In act S417, original/PHI dose information images are loaded from the greylist container to a file system via a greylist container downloading tool. S418 denotes a job involving a greylist container downloading process. S419 and S420 denote original dose information images. S421 denotes a PHI dose information image. S422 denotes a local file system. S423 and S424 denote a radiation dose structured report (RDSR). S425 denotes an original dose information image.

In act S426, PHI dose information images are generated from the original dose information images using a PHI validation tool (optional). In act S427, defects are validated by a receiver team. In act S428, PHI validation takes place. In act S429, error checking is performed.

If errors are present, in act S430, the defect is sent to the receiver team. If no errors are present, in act S431, a radiation dose structured report is generated from the original dose information images by an RDSR validation tool (optional). S432 denotes a job involving an RDSR validation process. In act S434, the defect is validated by a DM team.

In act S433, error checking is performed. If errors are present, in act S435, the defect is sent to the DM team. If errors are present, in act S436, a radiation dose structured report is generated from the PHI dose information images by an RDSR validation tool and the results are uploaded. S438 denotes a job involving an RDSR validation process.

In act S439, the scanner index is placed in the blacklist. In act S440, error checking is performed. If no errors are present, in act S441, the scanner index is placed in the whitelist and deleted from the blacklist. In act S442, the defect is received by an RCV team and deleted by it. S443 denotes a TFS defect. In act S444, the defect is received by a DM team and deleted by it.

Section A1 denotes an evaluation process, section A2 denotes a preparation process, section A3 denotes a validation process, and section A4 denotes a correction process.

Scanner index DICOM tags for obvious CT scanner dose information image variants may be defined as follows:

| DICOM tag | scanner index contribution |
| --- | --- |
| Manufacturer | scanner index-1 (SI-1) |
| Manufacturer model | scanner index-2 (SI-2) |
| Ward name | scanner index-3 (SI-3) |
| Photometric interpretation | scanner index-4 (SI-4) |
| Equipment serial number | scanner index-5 (SI-5) |
| Software version | scanner index-6 (SI-6) |

The scanner index becomes, for example:
scanner index='@'+'SI-1'+'@'+'SI-2'+'@'+'SI-3'+'@'+'SI-4'+'@'+'SI-5'+'@'+'SI-6'+'@'
Example=@Siemens@Definition Flash@CTAW3@Monochrome2@@Syngo VA30A@
The scanner index may have the following statuses:

| Status | Status change transition |
| --- | --- |
| "to be checked" | is set by the greylist uploader if a new scanner index for an operator is inserted into the table. |
| "in work" | is set by the greylist downloader if a greylist container has been downloaded to the file system. |
| "OK" | is set by the dose information image validator if a validation result was OK. |
| "not OK" | is set by the dose information image validator if a validation result was not OK. |

The following software modules run as independent programs.

"Greylist uploader": is invoked by the receiver whenever a new study is received by the picture archiving and communication system PACS.

"Greylist downloader": is cyclically invoked by a virtual machine or cloud service to process "to be checked" whitelist entries.

"Dose information image validation": is invoked by the greylist downloader during processing of a whitelist entry to be checked.

"Whitelist-browserHTML5-App": Mobile application for checking current whitelist/blacklist entry statuses.

The greylist uploader carries out the following acts. In act U0, the greylist uploader of the remote operator is cyclically started, e.g., every hour. In act U1, each local study directory in the receiver's request study pool is searched for (e.g., is obtained by the remote receiver). In act U2, each dose information image within a found local study directory is searched for (e.g., is obtained by the remote receiver). In act U3, the scanner index of this dose information image is received (e.g., is obtained by the remote receiver). In act U4, the scanner index of a new available dose information image (e.g., is obtained by the remote receiver) is compared with a whitelist in the central data repository to ascertain whether or not it contains the scanner index of that operator. In act U5, the complete directory with 1 . . . n files is uploaded from a local file system to the central data repository into a greylist container (e.g., if the greylist container does not exist, it is created). In act U6, the status of the new entry is set to "to be checked" and the scanner index is incorporated in the whitelist. In act U7, the container in the receiver's request study pool directory is deleted. In act U8, after a predefined waiting time, the process is continued with act U1.

The greylist downloader carries out the following acts. In act D0, the greylist downloader is cyclically started, e.g. every hour. In act D1, a scanner index line with the status="to be checked" is searched for in the whitelist/blacklist. In act D2, for each entry found, the greylist container reference (e.g., name) is obtained. In act D3, the complete container with 1 . . . n files is downloaded from the central data repository to the local file system directory (e.g., if the directory does not exist, it is created). In act D4, dose information image validation is performed and the results are entered both in the greylist container and in the whitelist/blacklist. In act D5, the complete local folder with 1 . . . n files is uploaded from the file system to the greylist container of the central repository (e.g., this has an updated status content in the whitelist/blacklist entries). In act D6, the status of the new entry is set to "OK" or "not OK" depending on the checking result in act D4 and this is entered in the whitelist. In act D7, the local folder is deleted if the container is in the request study pool directory. In act D8, the corresponding scanner index line is updated in the greylist container with the new status "in work". In act D9, the process is repeated by returning to act D2 until no values to be checked are found. In act D10, after a predefined waiting time, the process is initiated again with act D1.

The dose information image validator carries out the following acts. In act V0, begin dose information image validation, e.g. as a result of activating a greylist download mock (e.g., "for checking" or "not OK" on-demand activation).

In act V1, a search is conducted for the number of dose information images available in the local directory with a study content downloaded from the greylist container (e.g., "in work" or "not OK"). If original dose information images are available, acts D2-D7 may be applied to the previously transformed PHI-converted dose information images using a PHI transformation tool, and for all available dose information images a radiation dose structured report (RDSR) is called up via a Clunie tool and the RDSR is saved in the same local folder.

In act V2, the radiation dose structured report generated in act V1 is used and is converted to a text file via a dcmdump-DdmTK tool and saved in the same local folder. Then a text file "*_dcmtk_dcmdump.txt" generated in act V3 and an RDSR dose checking script is applied and the result is saved as a text file in the local folder.

In act V3, the result "*_Dose_Check.txt" is returned by the RDSR dose check to the local folder ("OK" or "not OK")

The software mechanism allows reliable and secure connection of CT scanners of different operators and different manufacturers to a cloud-based dose management system. This solves the problem of unifying non-standardized dose information images of CT scanners of different manufacturers. It may be provided that dose information images of CT scanners of different manufacturers are either supported or uploading of dose information images is suspended until issues are resolved. In addition, information about supported or unsupported dose information images of CT scanners is provided based on uniform criteria of a plurality of manufacturers.

The advantages lie in a cloud-enabled continuous runtime mechanism for supporting, in an automated and controlled manner, a linking of CT scanners that generate dose information images. A central cloud-enabled whitelist of CT scanner indices with tested dose information images is provided. A central cloud-enabled blacklist of CT scanner indices with dose information images that are currently not supported is provided. A scanner index may be defined as a table entry having a defined set of statuses (e.g., "for checking", "in work", "not OK" or "OK") within a cloud-enabled whitelist or blacklist.

An event-driven or cyclical runtime status/event machine that checks a local study folder containing dose information images that are not currently supported for scanner indexes in uploads of a whitelist/blacklist is on a greylist container in the cloud and sets a scanner index status to "to be checked".

An event-driven or cyclical runtime status/event machine that checks a greylist container in the cloud for scanner indices in uploads of a whitelist/blacklist is provided for support on a local study folder containing dose information images to be validated and sets a scanner index either to "OK" or "not OK".

The above object is achieved, as the whitelisting mechanism may be used for dose information images for a large base of CT scanners of different manufacturers to handle a reliable and effective operator connection to a cloud-based system.

Support for non-standardized dose information images for CT scanners of different manufacturers is standardized. Dose information images of different manufacturers may be either reliably supported or uploading of dose information images may be stopped until problems have been resolved. Information about supported or unsupported dose information images of different manufacturers may be provided based on uniform criteria.

All the features explained and shown in connection with individual embodiments may be provided in different combinations in the subject matter of the disclosure in order to simultaneously implement the advantageous effects thereof.

All the procedural acts may be implemented by devices that are suitable for carrying out the respective act. All the functions performed by the relevant features may be a procedural act of the method.

Although the disclosure has been illustrated and described in more detail by the exemplary embodiment, the disclosure is not limited by the disclosed examples and a person skilled in the art may derive other variations herefrom without departing from the scope of the disclosure.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for automatically controlling loading processes of dose information images, the method comprising:
    receiving a data record at a local data repository, the data record containing a dose information image and a scanner index;
    comparing the scanner index against a whitelist from a central data repository;
    transmitting the data record from the local data repository to a checking directory of the central data repository when the scanner index is not contained in the whitelist;
    validating the dose information image from the checking directory by character recognition; and
    entering the scanner index in the whitelist in an event of successful validation of the dose information image.

2. The method of claim 1, wherein the data record is transmitted from the local data repository to a non-checking directory of the central data repository when the scanner index is contained in the whitelist.

3. The method of claim 2, wherein the whitelist is stored in the central data repository.

4. The method of claim 3, wherein the whitelist is transmitted to the local data repository.

5. The method of claim 4, wherein the checking directory is cyclically scanned for new data records.

6. The method of claim 5, wherein uploading of data records to the non-checking directory is stopped when the scanner index is not contained in the whitelist.

7. The method of claim 6, wherein the data record is assigned a validation status.

8. The method of claim 2, wherein the whitelist is transmitted to the local data repository.

9. The method of claim 1, wherein the checking directory is cyclically scanned for new data records.

10. The method of claim 1, wherein uploading of data records to a non-checking directory is stopped when the scanner index is not contained in the whitelist.

11. The method of claim 1, wherein the data record is assigned a validation status.

12. The method of claim 1, wherein the validating is based on a correctness of dose information in the dose information image.

13. A system for automatically controlling loading processes of dose information images, the system comprising:
    an uploader configured to: (1) receive a data record at a local data repository, the data record containing a dose information image and a scanner index, (2) compare the scanner index against a whitelist from the central data repository, and (3) transmit the data record from the local data repository to a checking directory of the central data repository when the scanner index is not contained in the whitelist; and
    a validator configured to: (1) validate the dose information image using character recognition and (2) enter the scanner index in the whitelist in an event of successful validation of the dose information image.

14. The system of claim 13, wherein the system is configured to enter the scanner index in the whitelist when validation of the dose information image is successful.

15. A computer program product configured to be loaded into a memory of a computing device, wherein the computer program product comprises code sections configured to cause the computing device to perform:

receive a data record at a local data repository, the data record containing a dose information image and a scanner index;
compare the scanner index against a whitelist from a central data repository;
transmit the data record from the local data repository to a checking directory of the central data repository when the scanner index is not contained in the whitelist;
validate the dose information image from the checking directory by character recognition; and
enter the scanner index in the whitelist in an event of successful validation of the dose information image.

* * * * *